(12) United States Patent
Iida

(10) Patent No.: US 10,967,111 B2
(45) Date of Patent: Apr. 6, 2021

(54) BLOOD TREATMENT FILTER AND BLOOD BAG SYSTEM

(71) Applicant: TERUMO KABUSHIKI KAISHA, Tokyo (JP)

(72) Inventor: Naoki Iida, Shizuoka (JP)

(73) Assignee: Terumo Kabushiki Kaisha, Tokyo (JP)

(*) Notice: Subject to any disclaimer, the term of this patent is extended or adjusted under 35 U.S.C. 154(b) by 281 days.

(21) Appl. No.: 15/998,914

(22) PCT Filed: Feb. 15, 2017

(86) PCT No.: PCT/JP2017/005458
§ 371 (c)(1),
(2) Date: Aug. 16, 2018

(87) PCT Pub. No.: WO2017/141949
PCT Pub. Date: Aug. 24, 2017

(65) Prior Publication Data
US 2019/0343995 A1  Nov. 14, 2019

(30) Foreign Application Priority Data
Feb. 16, 2016  (JP) .............................. JP2016-026999

(51) Int. Cl.
*A61M 1/02* (2006.01)
*B01D 29/01* (2006.01)
*B01D 29/05* (2006.01)

(52) U.S. Cl.
CPC .......... *A61M 1/0218* (2014.02); *A61M 1/025* (2013.01); *A61M 1/0236* (2014.02);
(Continued)

(58) Field of Classification Search
CPC .............. A61M 1/0218; A61M 1/3635; A61M 1/0209; A61M 1/0236; A61M 1/025;
(Continued)

(56) References Cited

U.S. PATENT DOCUMENTS

2010/0108596 A1  5/2010  Duhaut et al.
2015/0265755 A1  9/2015  Lynn et al.

FOREIGN PATENT DOCUMENTS

| FR | 2677883 A1 | 12/1992 |
|---|---|---|
| JP | 09-510916 | 3/1995 |

(Continued)

OTHER PUBLICATIONS

WO2010026891A1 (EPO Machine Translation) (Year: 2020).*
(Continued)

*Primary Examiner* — Patrick Orme
(74) *Attorney, Agent, or Firm* — Terumo BCT, Inc. IP Law Dept (57) ABSTRACT

A blood treatment filter includes a housing having a first resin sheet and a second resin sheet, a filter member disposed in the housing, a peripheral edge molded body formed on a peripheral edge portion of the filter member and having an inner peripheral portion joined to an outer peripheral end edge of a filtering material, and a connection sheet extending outward from the peripheral edge molded body and connected to the housing.

9 Claims, 9 Drawing Sheets

(52) U.S. Cl.
CPC .......... *B01D 29/012* (2013.01); *B01D 29/05* (2013.01); *A61M 2202/0415* (2013.01); *A61M 2202/0427* (2013.01); *A61M 2202/0429* (2013.01); *A61M 2202/0439* (2013.01); *A61M 2207/00* (2013.01); *B01D 2201/30* (2013.01)

(58) Field of Classification Search
CPC .. A61M 2202/0415; A61M 2202/0427; A61M 2202/0429; A61M 2202/0439; A61M 2207/00; B01D 29/012; B01D 29/05; B01D 2201/30
See application file for complete search history.

(56) References Cited

FOREIGN PATENT DOCUMENTS

| | | | | |
|---|---|---|---|---|
| JP | 2004-130085 | A | 4/2004 | |
| JP | 2007135662 | A | 6/2007 | |
| JP | 4292428 | B2 | 7/2009 | |
| WO | WO-2010026891 | A1 * | 3/2010 | .......... A61M 1/3636 |
| WO | 2010026891 | A1 | 11/2010 | |

OTHER PUBLICATIONS

European Patent Office, European Search Report, EP17753205.8; dated Sep. 30, 2019, 7 pages.
International Searching Authority, International Search Report, PCT/JP2017/005458, dated Mar. 15, 2017, 4 pages.

* cited by examiner

BLOOD TREATMENT FILTER AND BLOOD BAG SYSTEM

TECHNICAL FIELD

The present invention relates to a blood treatment filter and a blood bag system used for separating and removing predetermined blood components such as, for example, leucocyte and platelet from blood.

BACKGROUND ART

Conventionally, blood treatment filters have been used to separate and remove predetermined blood components (for example, leucocyte and the like) from the blood collected from blood donors. The conventional blood treatment filter includes a housing made of a pair of resin sheets, a filter member provided between the pair of resin sheets to partition the interior of the housing into a blood inflow chamber and a blood outflow chamber, a blood inflow port communicating with the blood inflow chamber, and a blood outflow port communicating with the blood outflow chamber (see, for example, JP 4292428 B). The filter member is formed of a laminate of a plurality of filtering materials.

SUMMARY OF INVENTION

In manufacturing of the conventional blood treatment filter, a filter member is obtained by laminating a plurality of filtering materials and by sealing a peripheral edge portion of the laminate by, for example, high-frequency fusion, while pressurizing the peripheral edge portion in a thickness direction. However, in the filter member obtained in this way, since the filtering material is wrinkled, a portion in which the filtering material is not effectively used is generated. Also, since a hole structure is crushed at the sealed peripheral edge portion of the filter member, an effective area of the filtering material is reduced accordingly. Reduction in the effective area of the filtering material may cause a decrease in flow rate at the time of filtration, leucocyte leakage, clogging of filtration, hemolysis and the like. Furthermore, since the sealed peripheral edge portion is compressed to be thin and the filtering material is wrinkled as described above, there are problems such as creation of many extra gaps between the filter member and the housing, and occurrence of reduction in blood recovery rate due to residual blood.

The present invention has been made in view of the above problems, and an object of the present invention is to provide a blood treatment filter and a blood bag system capable of securing a large effective area of the filtering material and improving a blood recovery rate.

To achieve the above object, a blood treatment filter which removes a predetermined blood component from blood, the blood treatment filter includes: a housing having a first resin sheet and a second resin sheet constituting walls opposite to each other; a filter member which is provided between the first resin sheet and the second resin sheet, is provided with at least one filtering material, and partitions the interior of the housing into a blood inflow chamber and a blood outflow chamber; an inflow port communicating with the blood inflow chamber; an outflow port communicating with the blood outflow chamber; a peripheral edge molded body which is formed in a frame shape covering a peripheral edge portion of the filter member and has an inner peripheral edge portion joined to an outer peripheral end edge of the filtering material; and a connection sheet extending outward from the peripheral edge molded body and connected to the housing.

According to the blood treatment filter which adopts the above-described configuration, the inner peripheral portion of the peripheral edge molded body is joined to the outer peripheral end edge of the filtering material, and the collapse of the peripheral edge portion of the filter member is suppressed. Therefore, it is possible to prevent creation of wrinkles in the filter member, thereby preventing creation of a portion in which the filtering material is not effectively used due to wrinkles. Further, since the collapse of the peripheral edge portion of the filter member is suppressed, the hole structure at the peripheral edge portion is maintained and the filtering function can also be exhibited at the peripheral edge portion. Accordingly, a large effective area of the filtering material can be secured. Furthermore, since the collapse of the peripheral edge portion of the filter member is suppressed, an extra gap between the filter member and the housing can be reduced. Thus, it is possible to reduce the dead space in the housing, and to suppress a decrease in blood recovery rate due to residual blood.

In the above blood treatment filter, the connection sheet may be provided to surround the peripheral edge molded body, and the peripheral edge molded body may be connected to the first resin sheet and the second resin sheet via the connection sheet.

With this configuration, it is possible to connect the peripheral edge molded body and the housing with one connection sheet.

In the above blood treatment filter, the connection sheet may have a first connection sheet provided on the inflow port side, and a second connection sheet provided on the outflow port side, the first resin sheet may be connected to the peripheral edge molded body and the first connection sheet, and the second resin sheet may be connected to the peripheral edge molded body and the second connection sheet.

With this configuration, it is possible to further reduce the dead space in the housing and further effectively suppress the reduction of the blood recovery rate due to the residual blood.

In the above blood treatment filter, a ratio of an opening area of an opening exposing the surface of the filter member in the peripheral edge molded body to an area of a main surface of the filter member may be 95 to 100%.

Thus, since substantially the entire surface of the main surface of the filter member is exposed, it is possible to more effectively secure a large effective area of the filtering material.

In the above blood treatment filter, a thickness of the filtering material in the peripheral edge portion with respect to a thickness of the filtering material in a portion of the filter member other than the peripheral edge portion may be 90 to 100%.

As a result, since the filtering material is hard to collapse, it is possible to more effectively secure a large effective area of the filtering material.

Further, a blood bag system of the present invention includes: the above blood treatment filter; a first bag which is connected to the inflow port of the blood treatment filter via an inlet side tube to store the blood before being treated by the blood treatment filter; and a second bag which is connected to the outflow port of the blood treatment filter via an outlet side tube to store the blood treated by the blood treatment filter.

According to the blood treatment filter and the blood bag system of the present invention, a large effective area of the filtering material can be secured and the blood recovery rate can be improved.

DESCRIPTION OF EMBODIMENTS

Preferred embodiments of the present invention will be described below with reference to the accompanying drawings.

Figure 1:
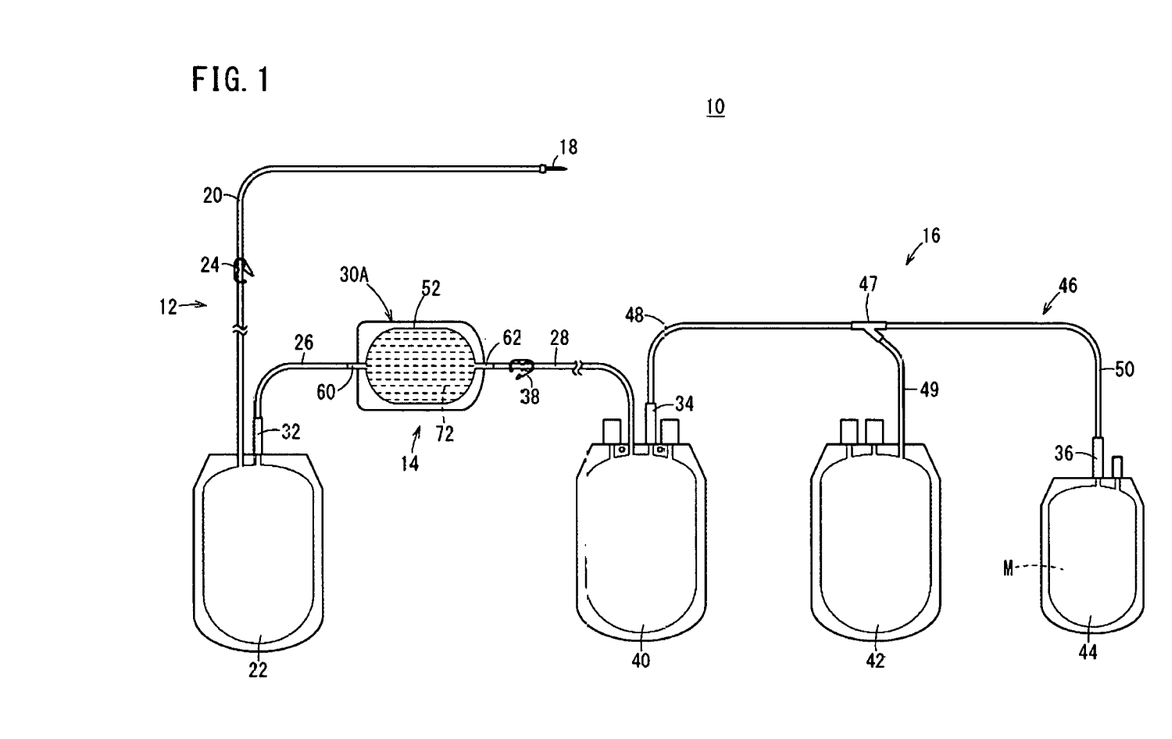
FIG. 1 is an overall schematic view of a blood bag system.

A blood bag system 10 illustrated in FIG. 1 centrifugally separates blood containing a plurality of components into a plurality of components having different specific gravities (for example, two components of a light specific gravity component and a heavy specific gravity component), and separately accommodates and stores each component in different bags.

The blood bag system 10 according to this embodiment is configured to centrifugally separate residual blood components when leucocyte and platelet are removed from whole blood, into two components of plasma and concentrated erythrocyte, and separately accommodate and store plasma and concentrated erythrocyte in different bags.

Specifically, the blood bag system 10 includes a blood sampling unit 12 which collects blood (whole blood) from a blood donor, a pretreatment unit 14 which removes a predetermined blood component from the whole blood, a separation treatment unit 16 which centrifugally separates the residual blood component when the predetermined components are removed into a plurality of blood components and accommodates (stores) the respective components in different bags.

The blood sampling unit 12 has a blood sampling needle 18, a blood sampling tube 20 having one end connected to the blood sampling needle 18, and a blood sampling bag 22 (a first bag) to which the other end of the blood sampling tube 20 is connected.

A clamp 24 that closes and opens a flow passage of the blood sampling tube 20 is provided in an intermediate portion of the blood sampling tube 20. Further, an initial flow blood bag for collecting the initial flow blood may be connected to the blood sampling tube 20 via a branching connector.

The blood sampling bag 22 is a bag for accommodating (storing) blood (whole blood) collected from the blood donor. It is preferable that an anticoagulant be contained in the blood sampling bag 22 in advance.

The blood sampling bag 22 is formed in a bag shape, by laminating a flexible sheet material made of a soft resin such as polyvinyl chloride and polyolefin, and fusing (heat fusion, high-frequency fusion) or adhering at a seal portion of the periphery thereof. Aparent bag 40, a child bag 42, and a chemical bag 44, which will be described later, are likewise formed in a bay shapo.

The pretreatment unit 14 includes a blood treatment filter 30A for removing predetermined cells, an inlet side tube 26 in which one end is connected to the blood sampling bag 22 and the other end is connected to an inlet (an inflow port 60 to be described later) of the blood treatment filter 30A, and an outlet side tube 28 in which one end is connected to an outlet (an outflow port 62 to be described later) of the blood treatment filter 30A and the other end is connected to the separation treatment unit 16.

In the present embodiment, the blood treatment filter 30A is configured as a leucocyte removal filter. Such a leucocyte removal filter has a structure in which a liquid permeable porous body having a large number of fine pores communicating from one side to the other side is accommodated inside a bag-like housing 52 formed of a soft resin sheet. In the present embodiment, the blood treatment filter 30A is configured to be also able to capture platelet. The detailed configuration of the blood treatment filter 30A will be described later.

The inlet side tube 26 is a tube for transferring the blood, which is collected from the blood donor, from the blood sampling bag 22 to the blood treatment filter 30A, and is connected to the upper part of the blood sampling bag 22. In the present embodiment, a sealing member 32 is provided at the end portion of the inlet side tube 26 on the side of the blood sampling bag 22. The sealing member 32 is configured so that the flow passage is closed in the initial state, but the flow passage is opened by performing the breaking operation. The same also applies to other sealing members 34 and 36 to be described later.

The outlet side tube 28 is a tube for transferring the residual blood components, when predetermined cells (leucocyte and platelet in the embodiment) are removed by the blood treatment filter 30A, to the separation treatment unit 16 (specifically, a parent bag 40 to be described later). A clamp 38 for closing and releasing the flow passage of the outlet side tube 28 is provided at an intermediate portion of the outlet side tube 28.

Next, the separation treatment unit 16 will be described. The separation treatment unit 16 includes a parent bag 40 (second bag) that accommodates (stores) the residual blood components when predetermined cells are removed by the blood treatment filter 30A, a child bag 42 for accommodating and storing the supernatant component obtained by centrifugally separating the blood components in the parent bag 40, a chemical bag 44 for accommodating an erythrocyte preservation solution M, and a transfer line 46 (the branching part 47 and a plurality of tubes 48 to 50) connected Lo the parent bag 40, the child bag 42 and the chemical bag 44

The parent bag 40 includes a bag for accommodating (storing) residual blood components (white blood removal) when predetermined cells are removed by the blood treatment filter 30A, and an erythrocyte bag for preserving a sedimentation component (concentrated erythrocytes) obtained by centrifugally separating the blood components.

The parent bag 40 and the tube 48 of the transfer line 46 are connected to each other via the sealing member 34. The child bag 42 is connected to the tube 49 of the transfer line 46. The chemical bag 44 and the tube 50 of the transfer line 46 are connected to each other via a sealing member 36.

Figure 2:
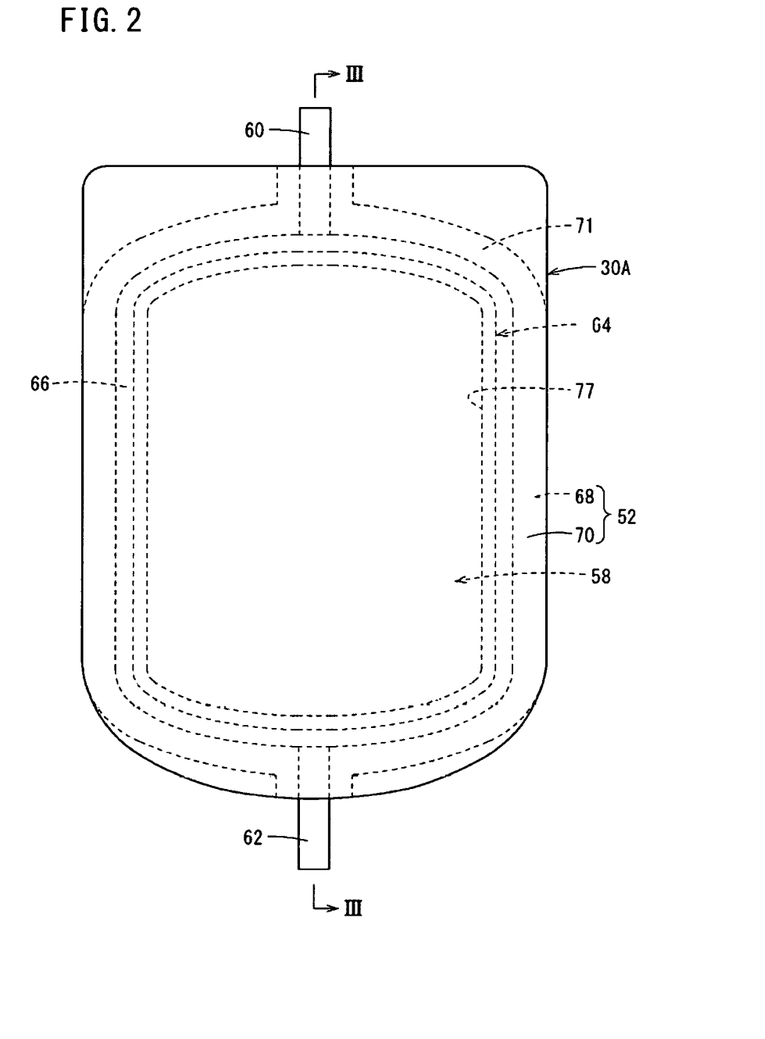
FIG. 2 is a plan view of a blood treatment filter.
Figure 3:
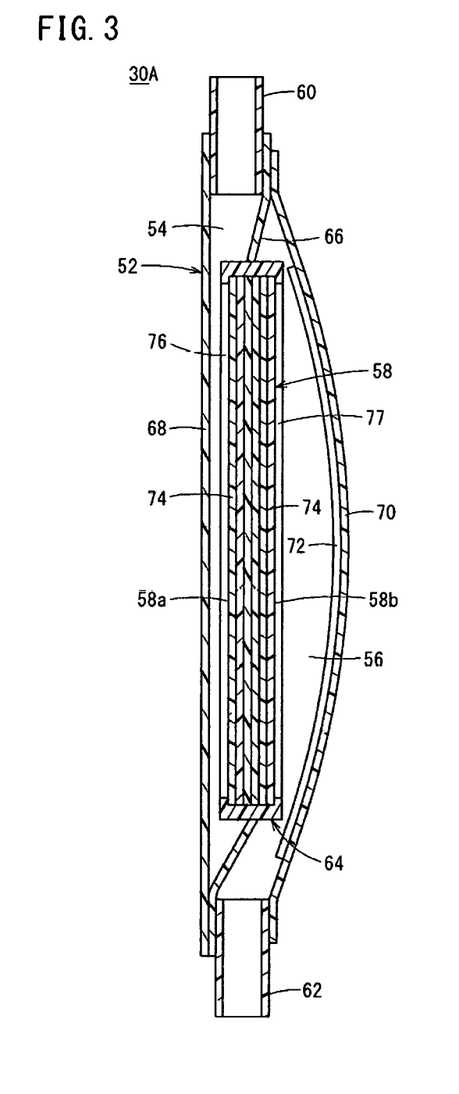
FIG. 3 is a cross-sectional view taken along the line III-III in FIG. 2.

As illustrated in FIGS. 2 and 3, the blood treatment filter 30A includes a housing 52 formed in a bag shape, a filter member 58 for partitioning the interior of the housing 52 into a blood inflow chamber 54 and a blood outflow chamber 56, an inflow port 60 communicating with the blood inflow chamber 54, an outflow port 62 communicating with the blood outflow chamber 56, a peripheral edge molded body 64 formed on the peripheral edge portion of the filter member 58, and a connection sheet 66 extending outward from the peripheral edge molded body 64.

The housing 52 is a bag-like container for containing blood to be treated (filtrated), and has a pair of resin sheets (a first resin sheet 68 and a second resin sheet 70) constituting walls opposite to each other. The first resin sheet 68 and the second resin sheet 70 are made of, for example, a soft resin such as polyvinyl chloride.

The peripheral edge portions of the first resin sheet 68 and the second resin sheet 70 are joined by fusion (a thermal fusion, an ultrasonic fusion or the like) via the connection sheet 66 over the entire circumference except for the inflow port 60 and the outflow port 62. In FIG. 2, a seal portion 71 is a joining portion provided by fusion of the first resin sheet 68, the second resin sheet 70 and the connection sheet 66.

As illustrated in FIG. 3, in order to make it easier to secure the flow passage on the side of the blood outflow chamber 56, on the side of the second resin sheet 70 facing the first resin sheet 68 (the side facing the filter member 58), a plurality of ribs 72 (see also FIG. 1) is provided. Ribs similar to the ribs 72 may also be provided on the side of the first resin sheet 68 facing the second resin sheet 70. The rib 72 may not be provided in the second resin sheet 70.

The filter member 58 is a member which is provided between the first resin sheet 68 and the second resin sheet 70, partitions the interior of the housing 52 into the blood inflow chamber 54 and the blood outflow chamber 56, serves as a flow passage when blood in the blood inflow chamber 54 moves to the blood outflow chamber 56, and separates and removes predetermined blood components (leucocyte and the like). Specifically, the filter member 58 is formed by laminating a plurality of filtering materials 74 having the same shape in the thickness direction.

The filtering material 74 is made of a sheet-like porous body having a large number of minute continuous pores communicating from one side to the other side. Examples of such a porous body include a sponge sheet made of polyurethane, a nonwoven fabric and the like. The number of laminated sheets of the filtering material 74 is, for example, about 2 to 10 sheets. In the filter member 58 of FIG. 3, six filtering materials 74 are laminated. The number of filtering materials 74 constituting the filter member 58 may be one.

The inflow port 60 is a member for allowing the blood to be treated to flow into the housing 52, and is made of, for example, a soft resin such as polyvinyl chloride. The inflow port 60 is sandwiched between the first resin sheet 68 and the connection sheet 66 at one end side of the housing 52 and is joined thereto by fusion.

The outflow port 62 is a member for allowing the treated blood to flow out of the housing 52 and is made of a soft resin such as polyvinyl chloride. The outflow port 62 is sandwiched between the second resin sheet 70 and the connection sheet 66 on the other end side of the housing 52 and is joined thereto by fusion.

The peripheral edge molded body 64 is a frame-shaped resin member formed by insert-molding. Specifically, the peripheral edge molded body 64 is formed to surround the peripheral edge portion of the filter member 58 over the entire circumference. The inner peripheral portion of the peripheral edge molded body 64 is joined to the outer peripheral edges of each of the plurality of filtering materials 74 which constitutes the filter member 58.

The peripheral edge molded body 64 is made of a soft resin such as polyvinyl chloride. The peripheral edge molded body 64 may be made of a mixture of a plurality of kinds of resins, for example, a mixed resin of polyvinyl chloride and polyurethane.

The peripheral edge molded body 64 has openings 76 and 77 which expose the surfaces of the filter member 58 opposite to each other. The sizes of the openings 76 and 77 of the peripheral edge molded body 64 are substantially the same as the sizes of the main surfaces 58a and 58b of the filter member 58. Specifically, a ratio (an area ratio) of the opening areas of the openings 76 and 77 of the peripheral edge molded body 64 to the areas of the main surfaces 58a and 58b of the filter member 58 is 95 to 100%, preferably, 98 to 100%. When the area ratio is 100%, the peripheral edge molded body 64 substantially holds the filtering material 74 with only the end surface (side surface) of the filtering material 74. In this case, the peripheral edge molded body 64 is fused with only the end surface of the filtering material 74.

Here, the "main surfaces 58a and 58b of the filter member 58" refers to surfaces substantially perpendicular to the thickness direction (lamination direction of the filtering material 74) of the filter member 58 in the filter member 58, that is, surfaces facing each of the first resin sheet 68 and the second resin sheet 70. Therefore, the areas of the main surfaces 58a and 58b of the filter member 58 can also be referred to as an area obtained by projecting the filter member 58 in its thickness direction.

In the process of molding the peripheral edge molded body 64, the peripheral edge portion of the filter member 58 is not compressed in the thickness direction, or is hardly compressed. That is, the thickness of the peripheral edge portion of the filter member 58 is the same (or substantially the same) as the thickness of the portions of the filter member 58 other than the peripheral edge portion. Specifically, the thickness of the filtering material 74 at the peripheral edge portion with respect to the thickness of the filtering material 74 at the portions other than the peripheral edge portion of the filter member 58 is 90 to 100%, preferably, 95 to 100%. The thickness of the filtering material 74 can be measured, for example, using a constant-pressure thickness measuring device. When a constant-pressure thickness measuring device for a soft material such as a soft foam material or flexible urethane foam is used, the thickness can be measured without crushing the filtering material 74.

The connection sheet 66 extending outward from the peripheral edge molded body 64 is connected to the housing 52. Accordingly, the peripheral edge molded body 64 is connected to the first resin sheet 68 and the second resin sheet 70 via the connection sheet 66.

In FIG. 3, the connection sheet 66 is formed to surround the peripheral edge molded body 64. The peripheral edge portion of one surface (the surface on the side of the first resin sheet 68) of the connection sheet 66 is joined to the first resin sheet 68 by fusion over the entire circumference except for the inflow port 60. The peripheral edge portion of the other side (the surface on the side of the second resin sheet 70) of the connection sheet 66 is joined to the second resin sheet 70 by fusion over the entire circumference except for the portion of the outflow port 62.

In FIG. 3, the connection sheet 66 is integrally formed with the peripheral edge molded body 64 by insert-molding. The connection sheet 66 may be a member joined to the peripheral edge molded body 64 by fusion, adhesion, or the like.

The blood treatment filter 30A configured as described above can be manufactured, for example, by the following method.

Figure 4A:
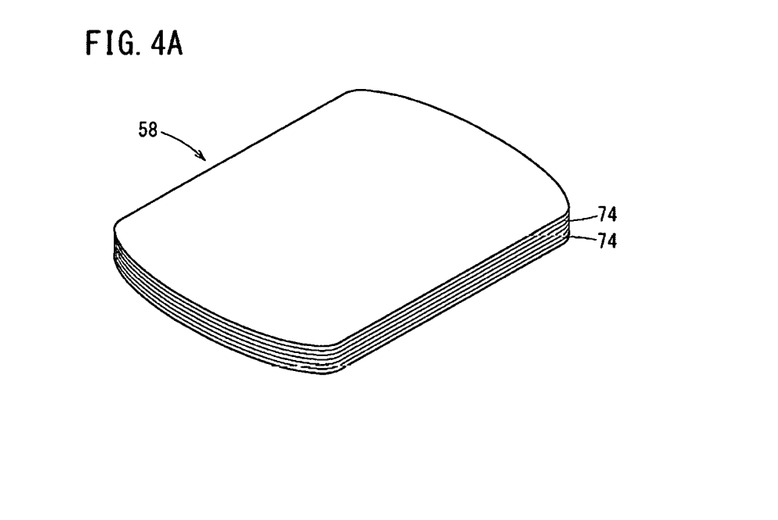
FIG. 4A is a diagram illustrating a process of providing a laminated filtering material.
Figure 4B:
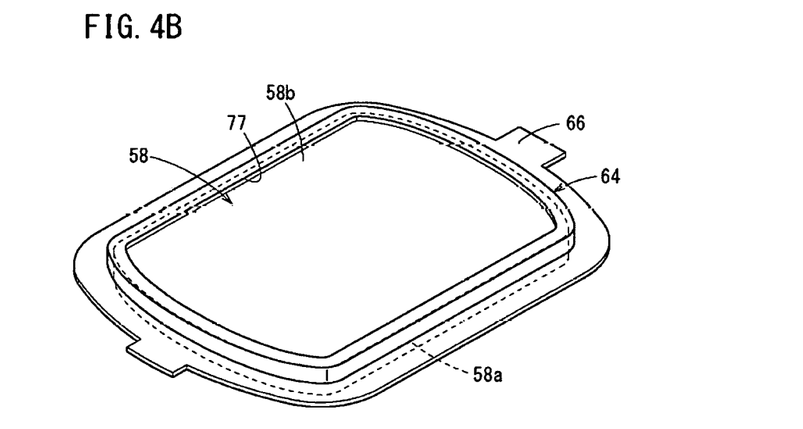
FIG. 4B is a diagram illustrating a peripheral edge molding process.

As illustrated in FIG. 4A, a plurality of laminated filtering materials 74 (filter members 58) of a predetermined shape is provided. For example, by laminating a plurality of materials of the filtering material 74 and punching the laminate in a predetermined shape in the thickness direction, the filter member 58 as illustrated in FIG. 4A is obtained. Next, as illustrated in FIG. 4B, a frame-shaped peripheral edge molded body 64 is formed on the peripheral edge portion of the filter member 58 by insert-molding (a peripheral edge molding process). In the present embodiment, the connection sheet 66 is also insert-molded integrally with the peripheral edge molded body 64 by the peripheral edge molding process.

In the peripheral edge molding process, the peripheral edge molded body 64 is formed so that the ratio of the opening areas of the openings 76 and 77 for exposing the surface of the filter member 58 in the peripheral edge molded body 64 with respect to the areas of the main surfaces 58a and 58b of the filter member 58 is 95 to 100% (preferably 98 to 100%), and the thickness of the filtering material 74 at the peripheral edge portion with respect to the thickness of the filtering material 74 at the portion other than the peripheral edge portion of the filter member 58 is 90 to 100% (preferably 95 to 100%).

Next, a housing molding process is performed. In the housing molding process, the filter member 58 having the peripheral edge molded body 64 formed at the peripheral edge portion thereof is disposed between the first resin sheet 68 and the second resin sheet 70, and the first resin sheet 68 and the second resin sheet 70 are joined by fusion to the peripheral edge molded body 64 via the connection sheet 66, thereby forming a housing 52 in which the interior is partitioned into the blood inflow chamber 54 and the blood outflow chamber 56 by the filter member 58.

When the first resin sheet 68 and the second resin sheet 70 are joined via the connection sheet 66, by joining them in a state in which the inflow port 60 is disposed between the first resin sheet 68 and the connection sheet 66, and the outflow port 62 is disposed between the second resin sheet 70 and the connection sheet 66, a housing 52 to which the inflow port 60 and the outflow port 62 are connected is obtained.

Thus, the blood treatment filter 30A having the configuration illustrated in FIGS. 2 and 3 is obtained.

Next, operations and effects of the blood treatment filter 30A and the blood bag system 10 configured as described above will be described.

In the use of the blood bag system 10 illustrated in FIG. 1, first, the blood sampling needle 18 is punctured into the blood vessel of the blood donor to collect the blood. Blood from the blood donor is accommodated in the blood sampling bag 22 via the blood sampling tube 20. At this time, since the sealing member 32 is not opened (a closed state of the flow passage), the outflow of blood from the blood sampling bag 22 to the inlet side tube 26 is prevented. Further, after the blood sampling is completed, the part of the blood sampling tube 20 near the blood sampling bag 22 is sealed by fusion with a tube sealer or the like, and the sealed portion is cut to separate the blood sampling needle 18 from the blood sampling bag 22.

Next, the sealing member 32 is broken to open the flow passage inside the sealing member 32, and the blood inside the blood sampling bag 22 is discharged to the inlet side tube 26. In FIG. 3, the discharged blood flows into the blood inflow chamber 54 from the inflow port 60 of the blood treatment filter 30A via the inlet side tube 26. In this case, for example, the blood sampling bag 22 is suspended from a stand or the like and placed at a high place, and blood is transferred using a fall (gravity).

Further, the blood flowing into the blood inflow chamber 54 moves to the blood outflow chamber 56 via the filter member 58. At this time, since a plurality of filtering materials 74 is present in the flow passage of blood, leucocyte and platelet in the blood are removed by the plurality of filtering materials 74. The blood from which leucocyte and platelet have been removed flows out of the outflow port 62 and is introduced into the parent bag 40 via the outlet side tube 28 illustrated in FIG. 1.

After the blood is accommodated in the parent bag 40, the part of the outlet side tube 28 near the parent bag 40 is sealed by fusion with a tube sealer or the like, and the sealed portion is cut to separate the blood sampling bag 22 and blood treatment filter 30A from the parent bag 40. Further, the parent bag 40 is centrifugally separated together with the child bag 42 and the chemical bag 44 to separate the blood in the parent bag 40 into an erythrocyte layer and a plasma layer. The separated plasma is transferred to the child bag 42 and stored therein. An erythrocyte preservation solution M in the chemical bag 44 is transferred into the parent bag 40 and added to the erythrocyte remaining in the parent bag 40.

In this case, according to the blood treatment filter 30A described above, as illustrated in FIG. 3, a peripheral edge molded body 64 is formed by insert-molding in the peripheral edge portion of the filter member 58, and the inner peripheral edge portion of the peripheral edge molded body 64 is joined to the outer peripheral edges of each of the plurality of filtering materials 74. Accordingly, it is possible to prevent creation of wrinkles on the filter member 58 (the filtering material 74), thereby preventing creation of a portion in which the filtering material 74 is not effectively used due to wrinkles.

Further, since the collapse of the peripheral edge portion of the filter member 58 is suppressed, the hole structure at the peripheral edge portion is maintained. Thus, the filtering function can also be exhibited at the peripheral edge portion of the filter member 58. In addition, since the openings 76 and 77 of the peripheral edge molded body 64 have substantially the same size as the main surfaces 58a and 58b of the filter member 58, a large effective area of the filtering material can be secured. Therefore, it is possible to suppress the occurrence of a decrease in the flow rate at the time of filtration, leucocyte leakage, clogging of filtration, hemolysis and the like.

Further, since the collapse of the peripheral edge portion of the filter member 58 is suppressed, an extra gap between the filter member 58 and the housing 52 can be reduced. This makes it possible to reduce a dead space inside the housing 52 and to suppress a decrease in blood recovery rate due to residual blood.

In particular, the ratio of the opening areas of the openings 76 and 77 for exposing the surface of the filter member 58 in the peripheral edge molded body 64 with respect to the areas of the main surfaces 58a and 58b of the filter member 58 is 95 to 100%. As a result, since substantially the entire surfaces of the main surfaces 58a and 58b of the filter member 58 are exposed, it is possible to more effectively secure a large effective area of the filtering material.

Further, the thickness of the filtering material 74 at the peripheral edge portion with respect to the thickness of the filtering material 74 at the portion of the filter member 58 other than the peripheral edge portion is 90 to 100%. As a result, since the filtering material 74 hardly collapses, it is possible to more effectively secure a large effective area of the filtering material.

In the blood treatment filter 30A, the connection sheet 66 is provided to surround the peripheral edge molded body 64, and the peripheral edge molded body 64 is connected to the first resin sheet 68 and the second resin sheet 70 via the connection sheet 66. With this configuration, the peripheral edge molded body 64 and the housing 52 can be connected by one connection sheet 66.

In the blood bag system 10 illustrated in FIG. 1, any one of the blood treatment filters 30B to 30E illustrated in FIGS. 5 to 9 may be adopted instead of the blood treatment filter 30A.

Figure 5:
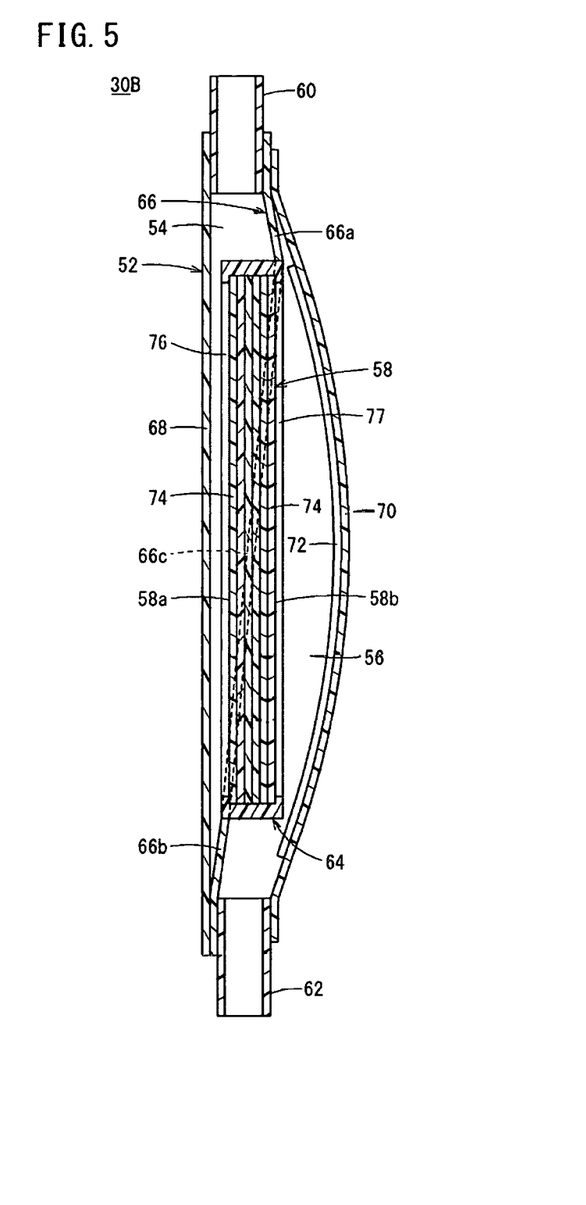
FIG. 5 is a cross-sectional view of a blood treatment filter of another configuration.

In the blood treatment filter 30B illustrated in FIG. 5, a portion 66*a* of the connection sheet 66 on the side of the inflow port 60 extends from the second resin sheet 70 side of the peripheral edge molded body 64. On the other hand, a portion 66*b* of the connection sheet 66 on the side of the outflow port 62 extends from the first resin sheet 68 side of the peripheral edge molded body 64. Further, in the connection sheet 66, the portion 66*c* extending from an end portion of the peripheral edge molded body 64 on the side of the inflow port 60 to the end portion on the side of the outflow port 62 is inclined to the first resin sheet 68 side, from the inflow port 60 side toward the outflow port 62 side Other parts of the blood treatment filter 30B are configured in the same manner as the blood treatment filter 30A.

According to the blood treatment filter 30B configured as described above, like the blood treatment filter 30A, it is possible to secure a wide effective area of the filtering material can be secured, and to suppress a reduction in blood recovery rate due to residual blood. In particular, according to the blood treatment filter 30B, since the connection sheet 66 is inclined with respect to the filter member 58, the flow passage of blood at the time of filtration is suitably secured, and the flow of blood in the housing 52 can be made further smooth.

Figure 6:
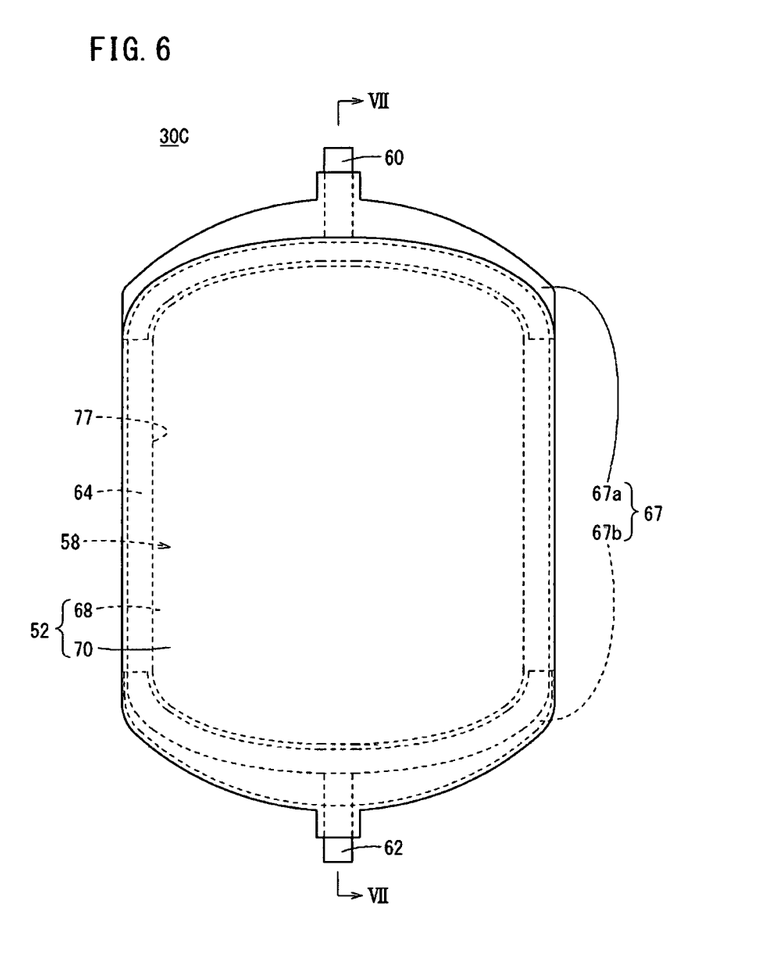
FIG. 6 is a plan view of a blood treatment filter of still another configuration.
Figure 7:
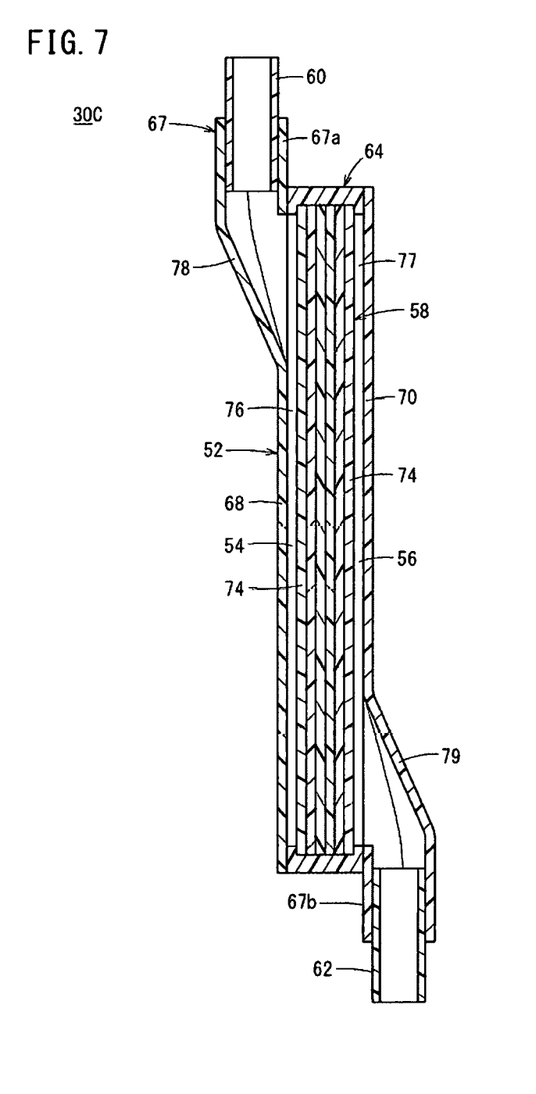
FIG. 7 is a cross-sectional view taken along line VII-VII of FIG. 6.

In the blood treatment filter 30C illustrated in FIGS. 6 and 7, the connection sheet 67 extending outward from the peripheral edge molded body 64 has a first connection sheet 67*a* provided on the inflow port 60 side, and a second connection sheet 67*b* provided on the outflow port 62 side. The first resin sheet 68 is connected to the peripheral edge molded body 64 and the first connection sheet 67*a*. The second resin sheet 70 is connected to the peripheral edge molded body 64 and the second connection sheet 67*b*.

As illustrated in FIG. 6, the first connection sheet 67*a* extends in a circular arc shape in the width direction along the portion of the peripheral edge molded body 64 on the side of the inflow port 60, and is joined to the peripheral edge portion of the first resin sheet 68 on the side of the inflow port 60 by fusion. Since the portion, of the peripheral edge portion of the first resin sheet 68, to which the first connection sheet 67*a* is joined is only the region on the side of the inflow port 60, most of the peripheral edge portion of the first resin sheet 68 is joined to the peripheral edge molded body 64.

The second connection sheet 67*b* extends in a circular arc shape in the width direction along a portion of the peripheral edge molded body 64 on the side of the outflow port 62, and is joined to the peripheral edge portion of the second resin sheet 70 on the side of the outflow port 62 by fusion. Since the portion, of the peripheral edge portion of the second resin sheet 70, to which the second connection sheet 67*b* is joined is only the region on the side of the outflow port 62, most of the peripheral edge portion of the second resin sheet 70 is joined to the peripheral edge molded body 64.

As illustrated in FIG. 7, in the end portion region of the housing 52 on the side of the inflow port 60, at a position other than the peripheral edge portion of the first resin sheet 68, the first resin sheet 68 and the first connection sheet 67*a* are not joined to each other. Thus, the bag structure 78 provided by the first resin sheet 68 and the first connection sheet 67*a* is formed in this region. Further, in the end portion region of the housing 52 on the side of the outflow port 62, at a position other than the peripheral edge portion of the second resin sheet 70, the second resin sheet 70 and the second connection sheet 67*b* are not joined to each other. Thus, a bag structure 79 provided by the second resin sheet 70 and the second connection sheet 67*b* is formed in this region.

In FIG. 7, the first connection sheet 67*a* and the second connection sheet 67*b* are configured as separate members from the peripheral edge molded body 64. Further, the first connection sheet 67*a* and the second connection sheet 67*b* may be portions integrally molded with the peripheral edge molded body 64.

Other parts of the blood treatment filter 30C are configured in the same manner as the blood treatment filter 30A.

According to the blood treatment filter 30C configured as described above, like the blood treatment filter 30A, it is possible to secure a wide effective area of the filtering material, and it is possible to suppress a decrease in blood recovery rate due to residual blood. In particular, according to the blood treatment filter 30C, most of the peripheral edge portion of the first resin sheet 68 is joined to the peripheral edge molded body 64, and most the peripheral edge portion of the second resin sheet 70 is joined to the peripheral edge molded body 64. This makes it possible to further reduce the dead space in the housing 52 and to more effectively suppress the decrease in blood recovery rate due to residual blood.

Figure 8:
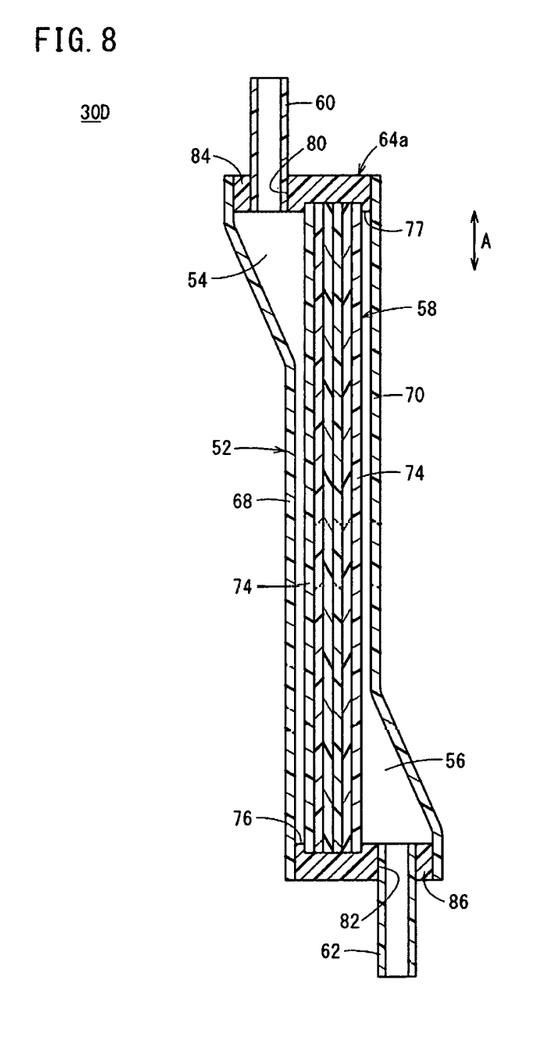
FIG. 8 is a cross-sectional view of a blood treatment filter of still another configuration.

In the blood treatment filter 30D illustrated in FIG. 8, the peripheral edge molded body 64*a* molded by insert-molding at the peripheral edge portion of the filter member 58 has a first communication hole 80 which allows the outer peripheral portion and the inner peripheral portion of the peripheral edge molded body 64*a* to communicate with each other and faces the blood inflow chamber 54, and a second communication hole 82 which allows the outer peripheral portion and the inner peripheral portion of the peripheral edge molded body 64*a* to communicate with each other and faces the blood outflow chamber 56.

One end portion of the peripheral edge molded body 64*a* has a first protruding portion 84 protruding toward the first resin sheet 68 side, and the first communication hole 80 is formed in the first protruding portion 84. The inflow port 60 is connected to the first communication hole 80.

The other end portion of the peripheral edge molded body 64*a* has a second protruding portion 86 protruding toward the second resin sheet 70 side, and the second communication hole 82 is formed in the second protruding portion 86. The outflow port 62 is connected to the second communication hole 82. The first communication hole 80 and the second communication hole 82 linearly penetrate in the wall thickness direction (the direction of arrow A) of the peripheral edge molded body 64*a*.

Further, other parts of the peripheral edge molded body 64*a* are configured in the same manner as the peripheral edge molded body 64. Other parts of the blood treatment filter 30D are also configured in the same manner as the blood treatment filter 30A.

According to the blood treatment filter 30D configured as described above, like the blood treatment filter 30A, it is possible to secure a wide effective area of the filtering material, and it is possible to suppress a decrease in blood recovery rate due to residual blood.

In particular, according to the blood treatment filter 30D, the inflow port 60 and the outflow port 62 are not sandwiched between the first resin sheet 68 and the peripheral edge molded body 64a, and between the second resin sheet 70 and the peripheral edge molded body 64a. Thus, the protruding portion provided by the inflow port 60 and the outflow port 62 are not formed on the joining surfaces of the first resin sheet 68 and the second resin sheet 70 with respect to the peripheral edge molded body 64a. Therefore, in the manufacturing process, it is easy to join the first resin sheet 68 and the second resin sheet 70 to the peripheral edge molded body 64a.

In the blood treatment filter 30D, only one of the first communication hole 80 and the second communication hole 82 may be formed linearly.

Figure 9:
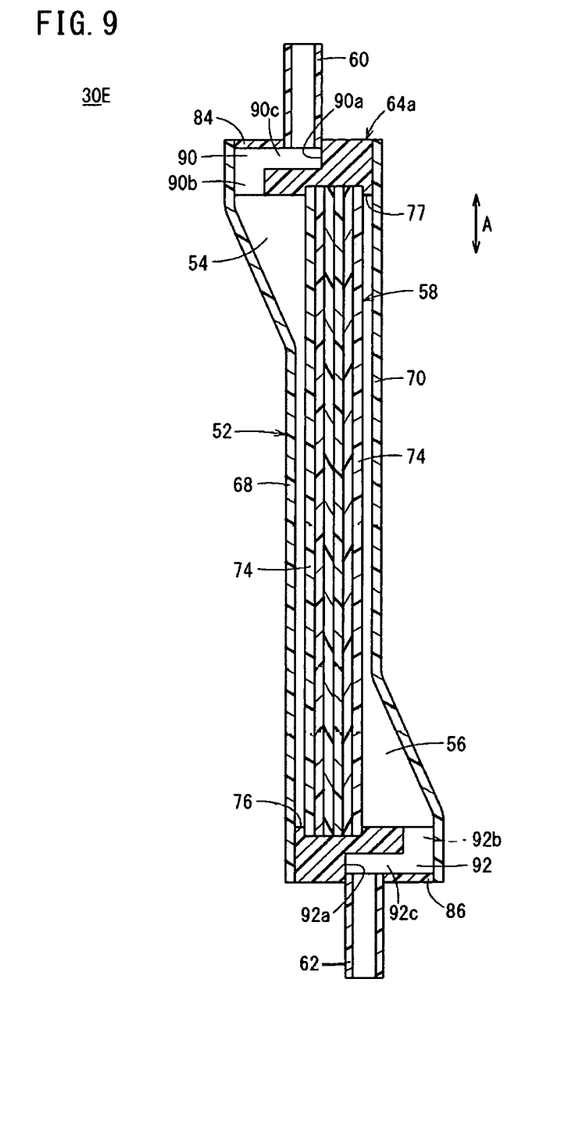
FIG. 9 is a cross-sectional view of a blood treatment filter of still another configuration.

A blood treatment filter 30E illustrated in FIG. 9 is a modified example of the blood treatment filter 30D illustrated in FIG. 8, and the shapes of a first communication hole 90 and a second communication hole 92 formed in the peripheral edge molded body 64a are different from the shapes (linear shapes) of the first communication hole 80 and the second communication hole 82 in the blood treatment filler 30D. Both the first communication hole 90 and the second communication hole 92 have a bent shape. In FIG. 9, both the first communication hole 90 and the second communication hole 92 are bent in a crank shape.

Specifically, the first communication hole 90 is configured to include a first outer path 90a extending in a wall thickness direction (a direction of an arrow A) of the peripheral edge molded body 64a and passing through the outer peripheral portion of the peripheral edge molded body 64a, a first inner path 90b extending in the wall thickness direction of the peripheral edge molded body 64a and passing through the outer peripheral portion of the peripheral edge molded body 64a, and a first intermediate path 90c extending along the thickness direction of the filter member 58 and allowing the first outer path 90a and the first inner path 90b to communicate with each other.

In the thickness direction of the filter member 58, the first outer path 90a is formed substantially at the center of the peripheral edge molded body 64a at a portion in which the first communication hole 90 is provided. On the other hand, the first inner path 90b is formed on the protruding end side of the first protruding portion 84 of the peripheral edge molded body 64a. Therefore, the first outer path 90a and the first inner path 90b are formed aL positions shifted in the thickness direction of the filter member 58.

The first inner path 90b has a form of a groove rather than a hole formed in the peripheral edge molded body 64a. By joining the first resin sheet 68 to the peripheral edge molded body 64a, a part of the first inner path 90b is covered with the first resin sheet 68. Thus, a flow passage extending from the inflow port 60 to the blood inflow chamber 54 is constructed.

The second communication hole 92 is configured to include a second outer path 92a extending in the wall thickness direction of the peripheral edge molded body 64a and penetrating the outer peripheral portion of the peripheral edge molded body 64a, a second inner path 92b extending in the wall thickness direction of the peripheral edge molded body 64a and passing through the outer peripheral portion of the peripheral edge molded body 64a, and a second intermediate path 92c extending along the thickness direction of the filter member 58 and allowing the second outer path 92a and the second inner path 92b to communicate with each other.

In the thickness direction of the filter member 58, the second outer path 92a is formed substantially at the center of the peripheral edge molded body 64a at the portion in which the second communication hole 92 is provided. On the other hand, the second inner path 92b is formed at the protruding end portion of the second protruding portion 86 of the peripheral edge molded body 64a. Accordingly, the second outer path 92a and the second inner path 92b are formed at positions shifted in the thickness direction of the filter member 58.

The second inner path 92b has a form of a groove rather than a hole formed in the peripheral edge molded body 64a. By joining the second resin sheet 70 to the peripheral edge molded body 64a, a part of the second inner path 92b is covered with the second resin sheet 70. As a result, a flow passage extending from the blood outflow chamber 56 to the outflow port 62 is constructed.

According to the blood treatment filter 30E configured as described above, like the blood treatment filter 30A, it is possible to secure a wide effective area of the filtering material, and it is possible to suppress a decrease in blood recovery rate due to residual blood.

In particular, according to the blood treatment filter 30E, since the first communication hole 90 and the second communication hole 92 have a bent shape, the opening (the first outer path 90a and the second outer path 92a) on the outer peripheral side of the peripheral edge molded body 64a can be provided at an arbitrary position.

The first inner path 90b of the first communication hole 90 and the second inner path 92b of the second communication hole 92 have a groove shape that faces the respective protruding end surfaces of the first protruding portion 84 and the second protruding portion 86. Therefore, when the peripheral edge molded body 64a is molded by insert-molding, the first communication hole 90 and the second communication hole 92 that are bent can be easily formed, using a plurality of core pins having different movable directions.

In the blood treatment filter 30E, only one of the first communication hole 90 and the second communication hole 92 may be formed in a bent shape. In this case, the other of the first communication hole 90 and the second communication hole 92 may be formed linearly like the first communication hole 80 and the second communication hole 82 illustrated in FIG. 8.

The present invention is not limited to the above-described embodiments, and various modifications are possible within the scope that does not depart from the gist of the present invention.

The invention claimed is:

1. A blood treatment filter configured to remove a predetermined blood component from blood, the blood treatment filter comprising:
   a housing including a first resin sheet and a second resin sheet constituting walls opposite each other;
   a filter member provided between the first resin sheet and the second resin sheet forming a partition in the interior of the housing into a blood inflow chamber and a blood outflow chamber, the filter member including at least one filtering material;

an inflow port in communication with the blood inflow chamber;

an outflow port in communication with the blood outflow chamber;

a peripheral edge molded body configured to surround a peripheral edge portion of the filter member over its entire circumference, the peripheral edge molded body including an inner peripheral edge portion joined to an outer peripheral end edge of the filtering material; and a connection sheet connecting the peripheral edge molded body to the housing.

2. The blood treatment filter according to claim 1, wherein the connection sheet surrounds the peripheral edge molded body, and the peripheral edge molded body is connected to the first resin sheet and the second resin sheet via the connection sheet.

3. The blood treatment filter according to claim 1, wherein the connection sheet includes a first connection sheet provided on the inflow port side, and a second connection sheet provided on the outflow port side, the first resin sheet is connected to the peripheral edge molded body and the first connection sheet, and the second resin sheet is connected to the peripheral edge molded body and the second connection sheet.

4. The blood treatment filter according to claim 1, wherein a ratio of an opening area of an opening exposing the surface of the filter member in the peripheral edge molded body to an area of a main surface of the filter member is from 95% to 100%.

5. The blood treatment filter according to claim 1, wherein a thickness of the filtering material in the peripheral edge portion with respect to a thickness of the filtering material in a portion of the filter member other than the peripheral edge portion is from 90% to 100%.

6. A blood bag system comprising:
a blood treatment filter;
a first bag connected to an inflow port of the blood treatment filter via an inlet side tube to store the blood before being treated by the blood treatment filter; and
a second bag connected to an outflow port of the blood treatment filter via an outlet side tube to store the blood treated by the blood treatment filter, wherein the blood treatment filter includes a housing including a first resin sheet and a second resin sheet constituting walls opposite each other, a filter member provided between the first resin sheet and the second resin sheet forming a partition in the interior of the housing into a blood inflow chamber and a blood outflow chamber, the filter member including at least one filtering material, the inflow port in communication with the blood inflow chamber, the outflow port in communication with the blood outflow chamber, a peripheral edge molded body configured to surround a peripheral edge portion of the filter member over its entire circumference, the peripheral edge molded body including an inner peripheral edge portion joined to an outer peripheral end edge of the filtering material, and a connection sheet connecting the peripheral edge molded body to the housing.

7. A method of making a filtration device, the method including:
inputting, into a housing, a first resin sheet and a second resin sheet constituting walls opposite one another;
fusing peripheral portions of the first resin sheet and the second resin sheet via a connection sheet;
providing a filter member between the first resin sheet and the second resin sheet forming a partition in the interior of the housing between a blood inflow chamber and a blood outflow chamber;
providing a molded body configured to surround a peripheral edge portion of the filter member over its entire circumference;
providing a blood inflow port in fluid connection with the blood inflow chamber; and
providing a blood outflow port in fluid connection with the blood outflow chamber.

8. The method of claim 7, wherein the filter member is laminated.

9. The method of claim 8, wherein the laminated filter member comprises a plurality of filtering materials.

* * * * *